United States Patent [19]

Magnusson et al.

[11] Patent Number: 4,933,510

[45] Date of Patent: Jun. 12, 1990

[54] PROPANOL DERIVATIVES

[75] Inventors: Hans G. Magnusson, Lund; Torbjörn Frejd, Södra Sandby, both of Sweden

[73] Assignee: Symbicom Aktiebolag, Umea, Sweden

[21] Appl. No.: 323,245

[22] Filed: Mar. 13, 1989

Related U.S. Application Data

[63] Continuation of Ser. No. 183,446, Apr. 13, 1988, abandoned, which is a continuation of Ser. No. 916,515, Sep. 3, 1986, abandoned.

[30] Foreign Application Priority Data

Jan. 14, 1985 [DK] Denmark .............................. 177/85
Jan. 13, 1986 [WO] PCT Int'l Appl. ................... PCT/DK86/00005

[51] Int. Cl.$^5$ ...................... C07L 31/36; C07L 69/76;

[52] U.S. Cl. ................................. 568/844; 260/410.6; 260/410.9 R; 260/408; 260/399; 556/428; 556/437; 556/485; 360/266; 360/263; 360/111; 360/112; 510/106; 510/20; 549/423; 549/420; 549/416; 558/1; 558/52

[58] Field of Search ..................... 568/844; 260/410.6, 260/410.9, 408, 399; 556/428, 437, 485; 560/266, 263, 111, 112, 102, 20; 549/423, 420, 416; 558/51, 52

[56] References Cited

U.S. PATENT DOCUMENTS 3,856,535 12/1974 Ferguson ............................. 106/18
4,016,200 4/1977 Onada et al. ........................ 568/800
4,868,289 9/1989 Magnusson et al. .

OTHER PUBLICATIONS

Shikmamedbekova et al C.A. 67 1967 81763j Uch. Zap. Azerb. Gos. Univ., Ser. Khim. Nauk 1966(1), 54–63.
McOmie, Ad/anus in Organic Chemistry, vol. 3, 1963, Interscience Publishers, New York, pp. 216–217.
"Comprehensive Organic Chemistry: The Synthesis and Reactions of Organic Compounds", Barton and Ollis, vol. 3, Sulphur, Selenium, Silicon, Boron, Organometallic Compounds.

Primary Examiner—Howard T. Mars
Attorney, Agent, or Firm—Iver P. Cooper

[57] ABSTRACT

Propanol derivatives of formula (I) wherein X is a leaving group; $R_1$ is H or a protecting group; and $R_2$ is H, and $R_3$ is a group—$CH_2Y$ wherein Y is a leaving group; or $R_2$ and $R_3$ together form =$CH_2$. The propanol derivatives of the formula (I) are useful as multifunctional alkylating agents.

11 Claims, No Drawings

PROPANOL DERIVATIVES

This application is a file wrapper continuation of Ser. No. 07/183,446, now abandoned under Rule 62, which was a file wrapper continuation of Ser. No. 06/916,515, now abandoned.

BACKGROUND OF THE INVENTION

1. Field of the Invention

The present invention relates to novel alkylating reagents useful as starting materials in organic synthesis.

2. Description of the Prior Art

Multifunctional compounds are of great value as starting materials in organic synthesis. Most of the simple, low-molecular weight compounds in this category are well known in the literature. Thus, a number of possible isomers of alcohols with the molecular formula $C_4H_8Br_2O$ have already been described (S. A. Pogorshelski, Chem. Zentralbl., 1, (1905), p 668).

There is, however, a need for novel, low-molecular, multifunctional compounds that may either facilitate the synthesis of known compounds by providing new synthetic routes or render it possible to prepare new structures.

SUMMARY OF THE INVENTION

One object of the present invention is to provide novel propanol derivatives useful as starting materials in organic synthesis.

Another object of the present invention is to provide a method for preparing the propanol derivatives of the invention.

The invention relates to propanol derivativs of the formula I

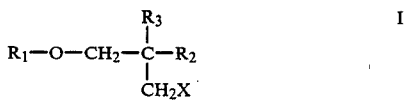

wherein X is a leaving group; $R_1$ is H or a protecting group; and $R_2$ is H, and $R_3$ is a group $—CH_2Y$ wherein Y is a leaving group; or $R_2$ and $R_3$ together form $=CH_2$.

In the present context, the term "leaving group" for X or Y designates any of the groups used in the art that are easily split off when the carbon atom, to which they are attached, is subjected to nucleophilic attack. Typical examples of leaving groups are halogens such as chlorine, bromine, and iodine, in particular bromine; p-toluene sulfonyloxy, methyl sulfonyloxy, ester functions such as $C_{1-8}$alkyl carbonyloxy, e.g. methyl carbonyloxy, ethyl carbonyloxy, propyl carbonyloxy, etc., and aryl ester functions such as phenyl carbonyloxy, wherein the phenyl group may optionally be substituted with electron-withdrawing groups such as nitro or fluoro.

The term "protecting group" for $R_1$ designates any group that on the one hand is able to prevent the oxygen atom, to which it is attached, from taking part in the substitution or elimination reactions, and on the other hand may be removed easily. Examples of such protecting groups are enol ethers (formed with ketones having α-protons); acyl such as $C_{1-8}$alkyl carbonyl, e.g. acetyl, propionyl, butyryl etc., and aryl carbonyl such as phenyl carbonyl wherein the phenyl groups may optionally be substituted with electron-withdrawing groups such as nitro or fluoro; silyl groups such as trimethylsilyl; tetrahydropyranyl; or a carbohydrate group.

The term "$C_{1-8}$alkyl" used above in connection with ester functions may designate such groups as methyl, ethyl, propyl, i-propyl, n-butyl, i-butyl, tert.butyl, pentyl, hexyl, and octyl.

When $R_2$ is H, and X and Y are different, the compounds of the formula I may appear in enantiomeric forms. Depending on the exact nature of the groups X, Y and $R_1$, these groups may also introduce stereoisomerism or diastereoisomerism into the compounds of the formula I. It is to be understood that the formula I encompasses all such stereoisomeric and diastereomeric forms.

In the subgroup of compounds of the formula I wherein $R_2$ is H, it is preferred that X and Y are identical, in particular selected from the leaving groups described above, especially halogens such as chlorine, bromine, or iodine, bromine being especially preferred.

It is preferred that the substituent $R_1$ is H since such compounds may act as nucleophiles.

Among the compounds of the formula I wherein $R_2$ and $R_3$ together form $=CH_2$, it is preferred that X is selected from the leaving groups described above, in particular halogens such as chlorine, bromine, and iodine, bromine being especially preferred.

Examples of preferred compounds are:
3-bromo-2-bromomethylpropan-1-ol
3-bromo-2-bromomethylprop-1-yl acetate
3-bromo-2-bromomethylprop-1-yl benzyl ether
3-bromo-2-bromomethylprop-1-yl tetrahydropyranyl ether
3-chloro-2-chloromethylpropan-1-ol
3-chloro-2-chloromethylprop-1-yl acetate
3-chloro-2-chloromethylprop-1-yl benzyl ether
3-chloro-2-chloromethylprop-1-yl tetrahydropyranyl ether
3-iodo-2-iodomethylpropan-1-ol
3-iodo-2-iodomethylprop-1-yl acetate
3-iodo-2-iodomethylprop-1-yl benzyl ether
3-iodo-2-iodomethylprop-1-yl tetrahydropyranyl ether
2-acetoxymethyl-3-bromo-prop-1-ene
2-benzyloxymethyl-3-bromo-prop-1-ene
2-tetrahydropyranyloxymethyl-3-bromo-prop-1-ene
2-hydroxymethyl-3-chloro-prop-1-ene
2-acetoxymethyl-3-chloro-prop-1-ene
2-benzyloxymethyl-3-chloro-prop-1-ene
2-tetrahydropyranyloxymethyl-3-chloro-prop-1-ene
2-hydroxymethyl-3-iodo-prop-1-ene
2-acetoxymethyl-3-iodo-prop-1-ene
2-benzyloxymethyl-3-iodo-prop-1-ene
2-tetrahydropyranyloxymethyl-3-iodo-prop-1-ene An especially preferred compound is 3-bromo-2-bromomethylpropan-1-ol.

The compounds of the formula I possess good properties as multifunctional reagents. Thus, if $R_1$ is H, the compound of the formula I is able to function as a good nucleophile under alkaline or acid conditions, and at the same time carry either one or two potential sites for nucleophilic attack, the number depending on whether $R_2$ is a group with $CH_2Y$ or whether $R_2$ and $R_3$ together form $=CH_2$. The compounds in which $R_2$ is a group $—CH_2Y$ can be reacted with a variety of nucleophilic reagents depending on the properties of the leaving groups X and Y. In this connection, mercapto ions are particularly interesting nucleophilic reagents.

The compounds in which $R_2$ and $R_3$ together form $=CH_2$ also have very interesting properties since the leaving group X is activated by the presence of the double bond. This activation makes it possible for such nucleophilic reagents as ketone or ester enolates, amines or alcohols to react easily with the compound of the formula I. Furthermore, the allylic alcohol derivatives formed after such alkylation reactions are useful as starting compounds in a Sharpless-epoxidation (cf. e.g. K. B. Sharpless, Org. Synth., 63)) whereby, through reaction with tert.butylhydroperoxide and e.g. Ti-[OCH(CH₃)₂]₄ and a 2R, 3R-tartrate, optically active compounds may be formed in high yield.

A particularly interesting use of the compounds of the formula I concerns the preparation of synthetic carbohydrate receptors such as those described in Applicant's copending application U.S. Ser. No. 06/907,690, entitled "Glycosidic Derivatives" filed on the same date as the present application, now issued as U.S. Pat. No. 4,868,289. In the compounds, the group $R_1$ in the formula I above is a receptor-active carbohydrate moiety, and the group X and optionally Y are replaced with various functional groups such as lipids, carriers, etc. Syntheses of this type are exemplified in Example 4 and 5.

The receptor-active carbohydrate moiety may be introduced into compounds of the formula I by reacting a compound of the formula I, wherein $R_1$ is H, with a derivative of the appropriate receptor-active carbohydrate having a leaving group at the reducing end of the carbohydrate. In this way, the receptor-active carbohydrate moiety is introduced in the place of the group $R_1$ in the formula I above. Following the introduction of the receptor-active carbohydrate moiety, various groups such as lipid groups, carriers etc. may be introduced in the place of the group X in the formula I above through reaction with appropiate nucleophilic derivatives of the groups to be introduced. Thus, thiols may be reacted with the carbohydrate moiety-containing compounds allowing the formation of bis-sulfides (when $R_2$ is H) and sulfides (when $R_2$ and $R_3$ together form $=CH_2$). The sulfides may optionally be oxidized to sulfoxides or sulfones. The compounds of the formula I containing the receptor-active carbohydrate moiety, in particular such compounds in which $R_2$ and $R_3$ together form $=CH_2$, may also be reacted with amines or alcohols as nucleophilic agents to form amines or ethers.

The present invention also relates to a process for preparing the propanol derivatives of the formula I defined above.

A process (a) for preparing compounds in which $R_2$ is H, and $R_3$ is $-CH_2Y$ comprises reducing the corresponding acid of the formula II

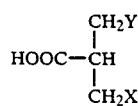

followed by optional protection of the hydroxy group formed.

The reduction may be performed by means of a wide variety of reducing agents such as NaBH₄ in water or protic or aprotic, polar or non-polar organic solvents such as methanol, ethanol, isopropanol, diglyme, benzene, toluene, ether, tetrahydrofuran, or 1,2-dimethoxyethane or by means of reducing agents such as diborane or LiAlH₄ in aprotic, polar or non-polar organic solvents such as benzene, toluene, ether, tetrahyrofuran, or 1,2-dimethoxyethane. The reduction may also be carried out by reducing the corresponding acid chloride or an ester by treatment with an alkali metal such as potassium, lithium, or sodium in liquid ammonia, by treatment with a hydride as mentioned above, or by treatment with a reducing complex such as Red-Al (Na-bis(2-methoxyethoxy)Al₂), the solvent being one of the previously mentioned solvents. The acid chloride or ester may also be subjected to a first reduction to the aldehyde, using hydrogen catalyzed by Pd/BaSO₄, followed by a second reduction to the alcohol, using NaBH₄. The reaction may be carried out at temperatures in the range from $-78°$ C. to $+150°$ C., normally from $0°$ C. to $50°$ C. such as room temperature, for a period of 0.1-48 hours, normally 8-24 hours such as 16 hours.

In a further process (b), propanol derivatives of the formula I wherein $R_2$ is H, and X and Y are halogen, are prepared by reacting a diol of the formula III

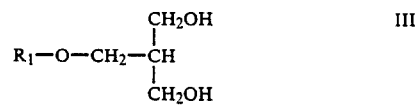

wherein $R_1$ is as defined above with a halogenating agent. The halogenating agent used may be any of the agents commonly used in the art such as thionyl chloride, phosphorous tribromide, or phosphorous pentabromide in e.g. pyridine, or triphenyl phosphine in CCl₄ or triphenyl phosphine in CBr₄. The reaction may be carried out at temperatures in the range from $-78°$ C. to $+200°$ C., normally from $0°$ C. to $100°$ C. such as the refluxing temperature of the solvent used, for 0.1-100 hours, normally 8-24 hours such as 16 hours. The preparation of iodides may be carried out by reacting the chlorides or bromides obtained above or e.g. the tosylate or the methane sulphonate with sodium iodide in refluxing acetone.

The diol of formula III may be prepared by protecting 2-hydroxymethyl-1,3-propandiol with an acetal group. Such an acetal group may be a benzylidene acetal group or an acetal group derived from a ketone such as cyclohexanone. A benzyliden acetal group may be established by reacting the triol with benzaldehyde and acid, or with α,α-dimethoxy toluene and acid. The acetal protected triol is then protected with $R_1$ after which the acetal function is removed by reaction with an acid such as hydrochloric acid.

A process (c) for the preparation of compounds of the formula I wherein $R_2$ and $R_3$ together form $=CH_2$ comprises subjecting a compound of the formula I wherein $R_2$ is H, and $R_3$ is $-CH_2Y$ to an elimination reaction. Such as elimination may suitably be carried out by treatment with a base such as an alkali metal hydroxide or carbonate, diazabicycloundecane, or diazabicyclononane. Examples of alkali metal hydroxides and carbonates are sodium hydroxide, potassium hydroxide, lithium hydroxide, cesium hydroxide, sodium carbonate, potassium carbonate, lithium carbonate and cesium carbonate, the treatment being carried out in e.g. dimethyl formamide, ethanol, or isopropanol. Treatment with the non-hydrophilic diaza bases may take place in aprotic solvents such ethyl acetate, methylene chloride, carbon tetrachloride, benzene, toluene, or ether. The reaction may take place at a temperature in the range from −78° C. to +150° C., normally from 0° C. to 100° C. such as room temperature, for a period of 0.1-24 hours, normally 8-24 hours such as 16 hours.

The process (c) may be carried out as part of the use for reacting with a nucleophile immediately before addition of the nucleophile, e.g. a thiole, an alcohol or an amine.

Another method (d) for preparing compounds of the formula I wherein $R_2$ and $R_3$ together form =$CH_2$ comprises reacting a carbonyl compound of the formula IV

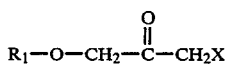
                                      IV with methylenetriphenylphosphorane. The reaction is a Wittig-reaction and is usually carried out in aprotic solvents such as ether or tetrahydrofuran at temperatures in the range from −78° C. to +150° C., normally from 0° C. to 100° C. such as the refluxing temperature of the solvent used, for a period of 0.1-72 hours, normally 8-24 hours such as 16 hours. The phosphorane compound is usually prepared from methyltriphenylphosphonium bromide by treatment with a strong base such as butyllithium.

The compounds of the formula I in which $R_2$ is H, and X and Y are p-toluene sulfonyloxy, methane sulfonyloxy, $C_{1-8}$alkyl carbonyloxy, or phenyl carbonyloxy may be prepared by a process (e) which comprises reacting the diol of formula III defined above with p-toluene sulphonyl chloride, methane sulphonyl chloride, a $C_{1-8}$alkyl carbonyl chloride, or a phenyl carbonyl chloride in a polar solvent such as pyridine at temperatures in the range from −78° C. to +150° C., normally from 0° C. to 100° C. such as the refluxing temperature of the solvent used, for a period of 0.1-24 hours, normally 8-24 hours such as 16 hours.

The invention is further illutrated by the following non-limiting examples.

EXAMPLE 1
3-Bromo-2-bromomethylpropan-1-ol (DlBol)

3-Bromo-2-bromomethylpropanoic acid (15.3 g; 62 mmol) (cf. A. F. Ferris, J. Org. Chem., 20 (1955) p 780) was dissolved in dry dichloromethane (400 ml) and cooled (0°). The reaction mixture was kept under nitrogen. A solution of diborane in tetrahydrofuran (190 ml; 190 mmol; 1M solution of $BH_3$ in THF) was added dropwise with stirring. After 1 hour, the cooling bath was removed and the mixture was left overnight at room temperature. Hydrochloric acid (210 ml; 1M) was added, the organic phase was separated and the aqueous phase was extracted with dichloromethane (3×50 ml). The combined organic phases were dried ($Na_2SO_4$) and concentrated. Flash chromatography of the residue gave pure DlBol (13.8 g; 96%). Bp ca. 45° C. (0.1 mm Hg); $n_D^{23}$ 1.5439;

IR-spectrum: $\nu_{max.}$=3340 cm$^1$
$^1$H-NMR (CDCl$_3$, Me$_4$Si) δ(ppm)=3.79 (d, 2 H, J=6.0 Hz, CH$_2$-O), 3.59 (d, 4 H, J=5.7 Hz, CH$_2$Br), 2.27 (heptet, 1 H, J=6 Hz, CH(CH$_2$)$_3$;
$^{13}$C-NMR (CDCl$_3$, Me$_4$Si): δ(ppm)=62.4 (CH$_2$OH), 44.4 (CH), 32.8 (CH$_2$Br);
Analysis calculated for C$_4$H$_8$Br$_2$O: C 20.7, H 3.48; Found: C 21.0, H 3.73.

EXAMPLE 2
3-Bromo-2-bromomethylpropan-1-yl acetate

3-Bromo-2-bromomethylpropan-1-ol (512 mg, 2.21 mmol), pyridin (10 ml), and acetic anhydride (10 ml) were stirred at room temperature for 17 h. The solvents were removed (co-evaporation with toluene), ethyl acetate (20 ml) was added and the solution was washed with water (2×10 ml). The aqueous phase was extracted with ethyl acetate (10 ml) and the combined organic phases were dried (Na$_2$SO$_4$) and concentrated. The residue was filtered through silica with heptane/ethyl acetate 4:1 to give the title acetate (483 mg, 81%), which had IR: $\nu_{max}$ 1752, 1230, 1050 cm$^{-1}$.
$^1$H-NMR-spectrum (CDCl$_3$, TMS): δ4.18 (d, 2H, J=6,4 Hz, AcOCH$_2$), 3.58, 3.3 (dABq, 4H, $J_{AB}$=10.6 Hz, J=5.3 Hz, J=6.2 Hz, CH$_2$—Br), 2.41 (heptet, 1H, CH), 2.09 (s, 3H, CH$_3$).

EXAMPLE 3
3-Bromo-2-bromomethylprop-1-yl-tetrahydropyranylether

3-Bromo-2-bromomethylpropan-1-ol (1.0 g, 4.3 mmol) and dihydropyran (1.81 g, 21.6 mmol) were dissolved in dry dichloromethane (20 ml) and cooled (0° C.). Toluene-p-sulfonic acid (10 mg) was dissolved in dichloromethane (2 ml) and added to the mixture. After 4 h, the cooling bath was removed and the reaction mixture was left at room temperature for 5.5 h. The mixture was cooled (0° C.) and an additional portion of toluene-p-sulfonic acid solution was added. After 7 h, toluene (30 ml) and ether (20 ml) were added and the mixture was washed with saturated sodium hydrogencarbonate solution (50 ml) and saturated sodium chloride solution (50 ml). The aqueous phases were extracted with toluene (50 ml) and the combined organic phases were dried (Na$_2$SO$_4$) and concentrated. The residue was distilled to give the title tetrahydropyranyl ether (1.07 g, 79%) (boiling point 85°-105° C., 0.08 mm Hg). Chromatography gave the pure compound (0.88 g, 65%) which had $n_D^{13}$ 1.5120; IR: $\nu_{max}$ 1130, 1060 cm$^{-1}$; MS (m/e) 85, 133, 135.
$^1$H-NMR-spectrum (CDCl$_3$, TMS): δ4.62 (t, 1H, J=3 Hz, O-CH-O) 3.75–3.90 (m, 2H), 3.40–3.70 (m, 6H), 2.35 (heptet, 1H, J~5 Hz, Br—CH$_2$—CH), 1.4-1.9 (m, 6H).
Analysis; calcd for C$_9$H$_{16}$Br$_2$O$_2$: C 34.2, H 5.10; Found: C 34.7, H 5.08.

EXAMPLE 4
Preparation of DlB glycosides using DlBol a starting material

Borontrifluoride etherate (0.7 ml) was added dropise with stirring to a solution of a fully acetylated sugar (1 mmol) and DlBol (232 mg; 1 mmol) in dichloromethane (3 ml) at room temperature. After 2-4 hours, the mixture was washed with water and sodium hydrogencarbonate solution, dried (Na$_2$SO$_4$), and concentrated. The residue was subjected to chromatography (SiO$_2$, ethyl acetate:hexane) to give the DlB glycoside in pure form. The following compounds were prepared:
3-Bromo-2-bromomethylprop-1-yl 2,3,46-tetra-O-acetyl-β-D-glucopyranoside (DlB-1). From 1,2,3,4,6-penta-O-acetyl-β-D-glucopyranose. Yield: 54%. $[α]_D^{23}$=−5° (c=0.6 in CDCl$_3$).
NMR-Spectrum (CDCl$_3$, TMS): δ (ppm)=5.22 (t, 1 H, $J_{2,3}$=$J_{3,4}$=9.7 Hz, H-3), 5.1 (t, 1 H, $J_{4,5}$=9.4 Hz, H-4), 4.99 (t, 1H, H-2), 4.51 (d, 1 H, $J_{1,2}=7.9$ Hz, H-1), 4.27, 4.15 (ABq with further coupling, each 1 H, $J_{AB}=12.6$ Hz, $J_{5,6}=4.0$ Hz, H-6,6'), 3.71 (m, 1 H, H-5), 2.34 (m, 1 H, CH(CH$_2$)$_3$).

Analysis calculated for $C_{18}H_{26}Br_2O_{10}$: C 38.5, H 4.66; Found: C 38.4, H 4.69.

3-Bromo-2-bromomethylprop-1-yl 2,3,4,6-tetra-O-acetyl-β-D-galactopyranoside (DlB-2). From 1,2,3,4,6-penta-O-acetyl-β-D-galactopyranose. Yield: 50%. $[\alpha]_D^{23}=+1°$ (c=0.7 in CDCl$_3$).

NMR-Spectrum (CDCl$_3$, TMS): δ (ppm)=5.40 (d, 1 H, $j_{3,4}=3.2$ Hz, H-4), 5.19 (dd, 1 H, $J_{2,3}=10.4$ Hz, H-2), 5.03 (dd, 1 H, H-3), 4.47 (d, 1 H, $J_{1,2}=7.6$ Hz, H-1), 4.19, 4.13 (ABq with further coupling, each 1 H, $J_{AB}=11.2$ Hz, $J_{5,6}=J_{5,6}=6.5$ Hz, H-6,6'), 3.92 (t, 1 H, $J_{4,5}=0.4$ Hz, H-5), 2.35 (septet, 1 H, J=5.8 Hz, CH(CH$_2$)$_3$).

EXAMPLE 5

Preparation of bi-sulfide glycosides using the compounds prepared in Example 4 as starting material A fully acetylated DlB glycoside (0.38 mmol), an alkyl thiol (1 mmol), cesium carbonate (338 mg; 1 mmol) and dimethylformamide (2 ml) were stirred at room temperature under nitrogen for 24-48 hours. The reaction was monitored by TLC (SiO$_2$, ethyl acetate:hexane). Dichloromethane (40 ml) was added and the mixture was washed with water (2×5 ml), dried (Na$_2$SO$_4$) and concentrated. Column chromatography (SiO$_2$, ethyl acetate:hexane) gave the pure, fully acetylated glycolipid.

The acetylated glycolipid (0.2 mmol) was dissolved in dichloromethane (15 ml) and methanolic sodium methoxide (10 ml; prepared by dissolving ca. 1 mg of sodium in methanol) was added. The reaction was monitored by TLC (chloroform:methanol:water, 65:35:10). In some cases, a precipitate was formed towards the end of the reaction. One drop of acetic acid was added and the reaction mixture was concentrated, suspended in water (10 ml) and freeze-dried to give a quantitative yield of the unprotected glycolipid, contaminated with a small amount of sodium acetate (ca. 1% w/w). The following compounds were prepared:

3-Hexadecylthio-2-hexadecylthiomethylprop-1-yl 2,3,4,6-tetra-O-acetyl-β-D-glycopyranoside (RSC16-1). From DlB-1 and hexadecanethiol. Yield: 70%. $[\alpha]_D^{23}=-1.6°$ (c=1.1 in CDCl$_3$).

NMR-Spectrum (CDCl$_3$, TMS): δ (ppm)=5.20 (t, 1 H, $J_{2,3}=9.3$ Hz, H-3), 5.06 (t, 1 H, $J_{3,4}=J_{4,5}=9.5$ Hz, H-4), 4.98 (dd, 1 H, H-2), 4.48 (d, 1 H, $J_{1,2}=7.9$ Hz, H-1), 4.26, 4.11 (ABq with further coupling, each 1 H, $J_{AB}=12.4$ Hz, $J_{5,6}=4.8$ Hz, $J_{5,6}=2.5$ Hz, H-6,6'), 2.6-2.4 (m, 8 H, CH$_2$—S).

Analysis calculated for $C_{50}H_{92}O_{10}S_2$: C 65.5, H 10.1; Found: C 65.7, H 10.2.

3-Hexadecylthio-2-hexadecylthiomethylprop-1-yl 2,3,4,6-tetra-O-acetyl-β-D-galactopyranoside (RSC16-2). From DlB-2 and hexadecanethiol. Yield: 79%. $[\alpha]_D^{23}=+1°$ (c=1.6 in CDCl$_3$).

NMR-Spectrum (CDCl$_3$, TMS): δ (ppm)=5.37 (dd, 1 H, $J_{4,5}=0.8$ Hz, H-4), 5.17 (dd, 1 H, $J_{2,3}=10.3$ Hz, H-2), 4.99 (dd, 1 H, $J_{3,4}=3.4$ Hz, H-3) 4.44 (d, 1 H, $J_{1,2}=7.8$ Hz, H-1), 2.7-2.4 (m, 8 H, CH$_2$—S).

Analysis calculated for $C_{50}H_{92}O_{10}S_2$: C 65.5, H 10.1; Found: C 65.3 H 10.2.

3-Hexadecylthio-2-hexadecylthiomethylprop-1-yl β-D-glucopyranoside (RSC16-8). From RSC16-1. $[\alpha]_D^{23}=-7°$ (c=0.9 in CMD).

NMR-Spectrum (CMD, TMS, 50°); δ (ppm)=4.29 (d, 1H, $J_{1,2}=7.6$ Hz, H-1), 2.70 (d, 4 H, J=6.4 Hz, CH-(CH$_2$-S)$_2$), 2.53 (t, 4 H, J=7.3 Hz, S—CH$_2$—CH$_2$).

3-Hexadecylthio-2-hexadecylthiomethylprop-1-yl β-D-galactopyranoside (RSC16-9). From RSC16-2. $[\alpha]_D^{23}=-3°$ (c=0.5 in CMD).

NMR-Spectrum (CMD, TMS, 20°): δ (ppm)=4.24 (virtual coupling, $J_{1,2}=7.6$ Hz, H-1), 2.71 (d, 4 H, J=6.7 Hz, CH—(CH$_2$—S)$_2$), 2.53 (t, 4 H, J=7.2 Hz, S—CH$_2$—CH$_2$).

We claim:

1. Compounds of the formula:

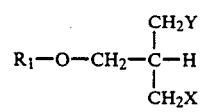

wherein X is a leaving group, Y is the same or a different leaving group, and R$_1$ is H or a protecting group selected from the group consisting of C$_{1-8}$ alkyl carbonyl, phenylcarbonyl, phenylcarbonyl wherein the phenyl moiety is substituted with nitro or fluoro, silyl or tetrahydropyranyl protecting groups.

2. The compound of claim 1 wherein X and Y are selected independently from the group consisting of halogen, p-toluenesulfonyloxy, methanesulfonyloxy, C$_{1-8}$ alkyl carbonyloxy, phenyl carbonyloxy, or phenyl carbonyloxy in which the phenyl moiety is substituted with nitro or fluoro.

3. The compound of claim 1 wherein X and Y are selected independently from the group consisting of chlorine, bromine an iodine.

4. The compound of claim 1 wherein R$_1$ is hydrogen.

5. The compound of claim 4 wherein X and Y are selected independently from the group consisting of halogen, p-toluenesulfonyloxy, methanesulfonyloxy, C$_{1-8}$ alkyl carbonyloxy, phenyl carbonyloxy, or phenylcarbonyloxy wherein the phenyl moiety is substituted with nitro or fluoro.

6. The compound of claim 4 wherein X and Y are selected independently from the group consisting of chlorine, bromine and iodine.

7. The compound of claim 1 wherein X and Y are the same leaving group.

8. The compound of claim 7 wherein X and Y are the same and are selected from the group consisting of halogen, p-toluenesulfonyloxy, methanesulfonyloxy, C$_{1-8}$ alkyl carbonyloxy, phenyl carbonyloxy, or phenylcarbonyloxy wherein the phenyl moiety is substituted with nitro or fluoro.

9. The compound of claim 7 wherein X and Y are the same and are selected from the group consisting of bromine, chlorine and iodine.

10. The compound of claim 7 wherein X and Y are both bromine and R$_1$ is a protecting group.

11. 3-Bromo-2-bromomethylpropan-1-ol.

* * * * *